(12) United States Patent
Gross et al.

(10) Patent No.: US 8,878,691 B2
(45) Date of Patent: Nov. 4, 2014

(54) METHOD FOR PROVIDING VISUALIZATION OF A DATA AGE

(75) Inventors: Brian Gross, North Andover, MA (US);
Soren S. Johnson, Wakefield, MA (US);
Gregory H. Raber, Sterling, MA (US);
Erik E. Johnson, Bedford, NH (US)

(73) Assignee: Koninklijke Philips N.V., Eindhoven (NL)

( * ) Notice: Subject to any disclaimer, the term of this patent is extended or adjusted under 35 U.S.C. 154(b) by 761 days.

(21) Appl. No.: 13/058,266

(22) PCT Filed: Aug. 11, 2009

(86) PCT No.: PCT/IB2009/053549
§ 371 (c)(1),
(2), (4) Date: Feb. 9, 2011

(87) PCT Pub. No.: WO2010/023578
PCT Pub. Date: Mar. 4, 2010

(65) Prior Publication Data
US 2011/0140912 A1    Jun. 16, 2011

Related U.S. Application Data

(60) Provisional application No. 61/092,462, filed on Aug. 28, 2008.

(51) Int. Cl.
G08C 19/16 (2006.01)
G08B 23/00 (2006.01)
G08C 15/06 (2006.01)
G08C 19/22 (2006.01)
H04Q 9/00 (2006.01)
A61B 5/00 (2006.01)
A61B 5/04 (2006.01)
G06F 19/00 (2011.01)

(52) U.S. Cl.
CPC .................................. *G06F 19/3406* (2013.01)
USPC ............ 340/870.02; 340/870.01; 340/870.07; 600/301; 600/522; 600/523

(58) Field of Classification Search
USPC ........ 340/870.01, 870.07; 600/300, 301, 316, 600/365, 508, 522, 523
See application file for complete search history.

(56) References Cited

U.S. PATENT DOCUMENTS

| 5,532,715 | A | | 7/1996 | Bates et al. |
| 5,622,178 | A | * | 4/1997 | Gilham ......................... 600/523 |
| 5,912,656 | A | | 6/1999 | Tham et al. |
| 6,322,516 | B1 | * | 11/2001 | Masuda et al. ................ 600/493 |
| 7,530,077 | B2 | * | 5/2009 | Bhogal et al. .................. 719/318 |

(Continued)

FOREIGN PATENT DOCUMENTS

| EP | 0764912 A2 | 3/1997 |
| GB | 1027320 | 9/1964 |

(Continued)

*Primary Examiner* — Hai Phan
*Assistant Examiner* — Franklin Balseca (57) ABSTRACT

Medical monitor readings (150) are displayed along with an indication of along with the age of the reading. The reading display is changed by altering the intensity of the reading value (210-240), color of the reading value (310-330), a subscript next to the reading (400), a shape of the background (600-700), or icon (FIGS. 6-11) to indicate the age of a presented reading.

19 Claims, 13 Drawing Sheets

(56) References Cited

U.S. PATENT DOCUMENTS

| | | | |
|---|---|---|---|
| 7,802,634 B2 * | 9/2010 | Boone | 175/45 |
| 2002/0133061 A1 * | 9/2002 | Manetta | 600/300 |
| 2004/0025113 A1 | 2/2004 | Penke et al. | |
| 2005/0275655 A1 | 12/2005 | Stolze et al. | |
| 2007/0159922 A1 * | 7/2007 | Zimmerman et al. | 367/103 |
| 2007/0167693 A1 * | 7/2007 | Scholler et al. | 600/301 |
| 2008/0097175 A1 * | 4/2008 | Boyce et al. | 600/323 |
| 2010/0223070 A1 | 9/2010 | Kelly et al. | |

FOREIGN PATENT DOCUMENTS

| | | | |
|---|---|---|---|
| JP | 59117047 A | 7/1984 | |
| JP | 2006255020 A | 9/2006 | |
| WO | 2007025341 A1 | 3/2007 | |
| WO | WO 2007025341 A1 * | 3/2007 | 600/479 |
| WO | 2008045538 A2 | 4/2008 | |

\* cited by examiner

METHOD FOR PROVIDING VISUALIZATION OF A DATA AGE

CROSS REFERENCE TO RELATED APPLICATIONS

This application claims the benefit of U.S. provisional application Ser. No. 61/092,462 filed Aug. 28, 2008, which is incorporated herein by reference.

The present application relates to the art of data display. It finds particular application to the display of aperiodically acquired physiological data and will be described with particular reference thereto. However, it will also find application in other types of displays in which the age of the data is of interest.

Patients in a medical setting typically have several physiological parameters monitored. Some, like ECG, SpO2 and invasive are continuously measured. Others, like non-invasive blood pressure, spot check temperature, and laboratory values, are only measured intermittently. The values of these and other physiological parameters are temporally relevant as they may have triggered treatment change, and are typically displayed on a monitor with a date and time stamp indicating when they were obtained.

Because the age of the intermittently measured parameter data is significant to the clinician, it is commonly marked with a sample acquisition date and time stamp, particularly the time when the parameter was measured. One problem with the time stamp is that the monitor display is already cluttered with the numerical values of numerous measured physiological parameters. Another problem is that the clinician performs mental math to see how old the measurement really is. In some instances, the clinician will also make a determination of whether and how much the age of the measurement affects the clinical value of the measurement.

The present application provides an improved method and apparatus which overcomes the above-referenced problems and others.

In accordance with one aspect, a method is presented for displaying a reading or data value. A reading or data value is displayed and the display is altered as the data value ages with time such that the display is indicative of the data value and its age.

In accordance with one aspect, an apparatus is presented that displays a reading or data value. The apparatus includes a human readable display device and a processor programmed to control the display device to display the reading or data value and alter the displayed reading or data value or a label progressively with time such that the displayed value or the table thereof is indicative of its age.

An advantage resides in reducing clutter, particularly a number of alphanumeric characters and symbols, on the face of a display device.

An advantage resides in enabling a clinician to quickly determine the age of each reading on a display screen without requiring the clinician to performing the mental arithmetic of by subtracting the time a the reading was taken from the current time now in order to calculate the age of a reading, and repeating this math for each reading on the display.

A further advantage is that it provides intuitive assessment of the clinical value of a reading on a display.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
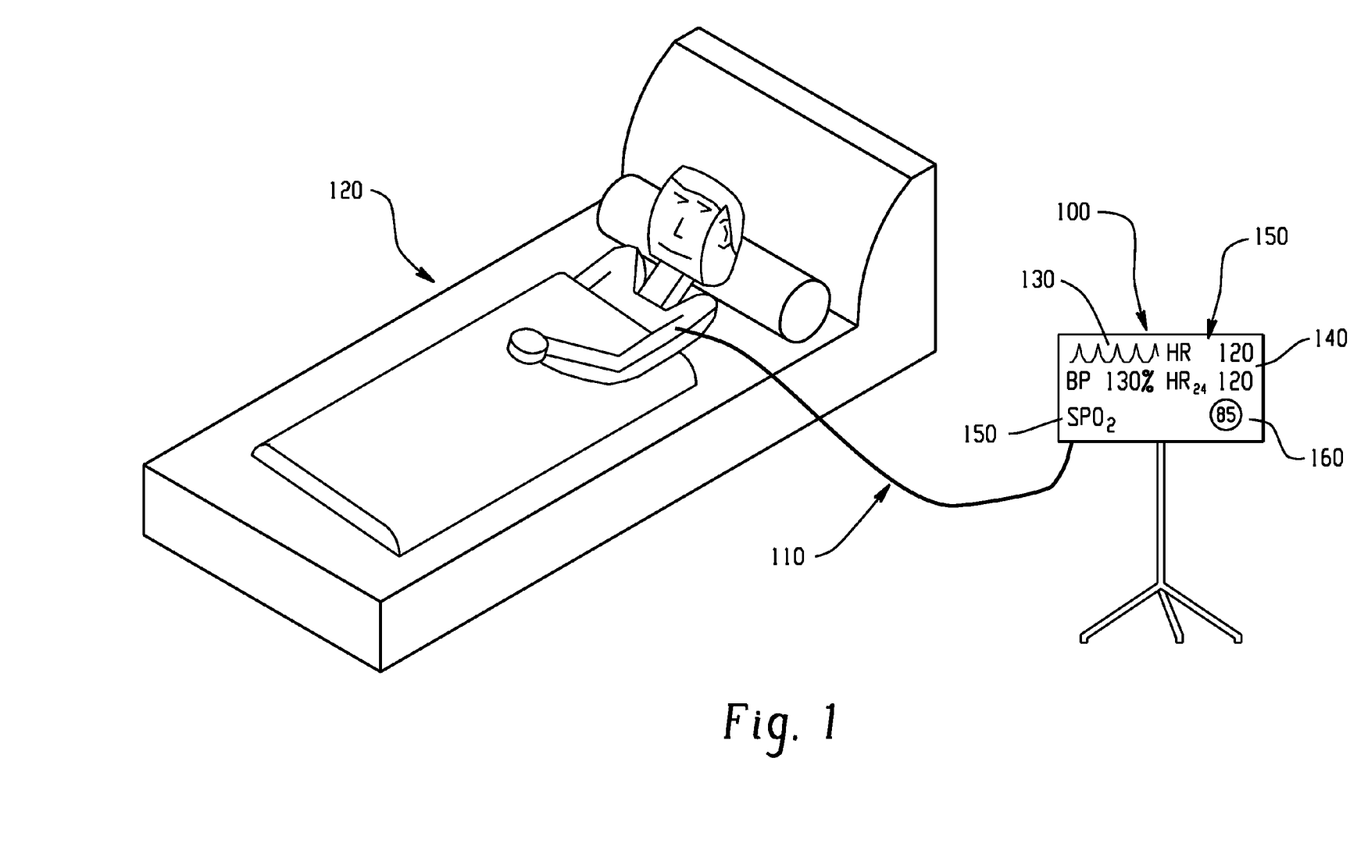
FIG. 1 illustrates the parameter display adjacent to the patient bed.

With reference to FIG. 1, a medical monitor for patients uses measurement devices that measure various physiological parameters and a display device 100 that displays values of the measurement parameters, commonly called readings. Such readings are gathered by an electronic probe or monitor 110 and displayed on a medical monitoring display 100 which is often located near a patient bed 120. The display presents some medical data as a graphical readout 130 and other readings and information in numbers 140, or text 150. Some readouts have a relevance which is time dependent. There is a need in the art of medical displays for a simple, intuitive means to measure and indicate how long ago the last data reading was taken. The present application presents a plurality of means by which the age of a data reading may be measured.

In one embodiment, the age of data displayed is conveyed by the color or intensity of the data 140. In another embodiment, the age of data is conveyed by use of a subscript next to the actual data reading which would indicate the number of days, hours, minutes, or seconds the reading has been displayed or could present the amount of time until the next reading is due. In another embodiment, the age of a data display is conveyed graphically 160 through use of an icon or symbol such as, but not limited to a clock or a circle with removable wedges, an hour glass, or the like. The picture or symbol represents the length of time the data has been displayed, will remain on display, or the length of time remaining until the next data reading is to be obtained. Use of such means may also reduce screen clutter.

Typically, bedside patient monitors and nursing station central monitors display a plurality of physiological parameters for each patient. Some of these parameters are measured continuously and in real time, and others are measured aperiodically. The aperiodic measurements may be taken every hour, every few hours, every day, etc. In order to inform the medical care giver how old each displayed aperiodic parameter is, it was common to place a date stamp in conjunction with the parameter title and number. The date stamp might be a time, or time and day at which the measurement was made. These additional numbers on an already-busy display add to clutter, making the display harder to read. Typically, the more data displayed, the more difficult it becomes for a user to read the display and sort out relevant data from not relevant data. Moreover, the care-giver has to do mental math to derive the age of the measurement from the time it was made.

The present application discloses a method and apparatus to display data and simultaneously inform the user how old, recent, and relevant the data is to the current clinical picture. Using a non-text based intuitive technique to convey the age of data without use of time and date stamps eliminates text from the display screen area and thereby reduces screen clutter. Relevance of data may be indicated based on a displayed parameter such as brightness, intensity, color intensity relative to the parameter label used in the real-time monitor, by use of a subscript or superscript located on either side of the value, or special icon as a background for the data parameter. As a new aperiodic parameter is measured, such as non-invasive blood pressure, it is displayed on the display of the monitor by an underlying parameter display algorithm. In some instances, the reading is displayed with a time stamp and the reading is automatically removed from the real time display after a preconfigured aging threshold. A threshold is a predetermined maximum time for which the data parameter should be displayed. An example would be that of a certain data value which should remain on the screen for one hour and then should be removed.

Figure 2:
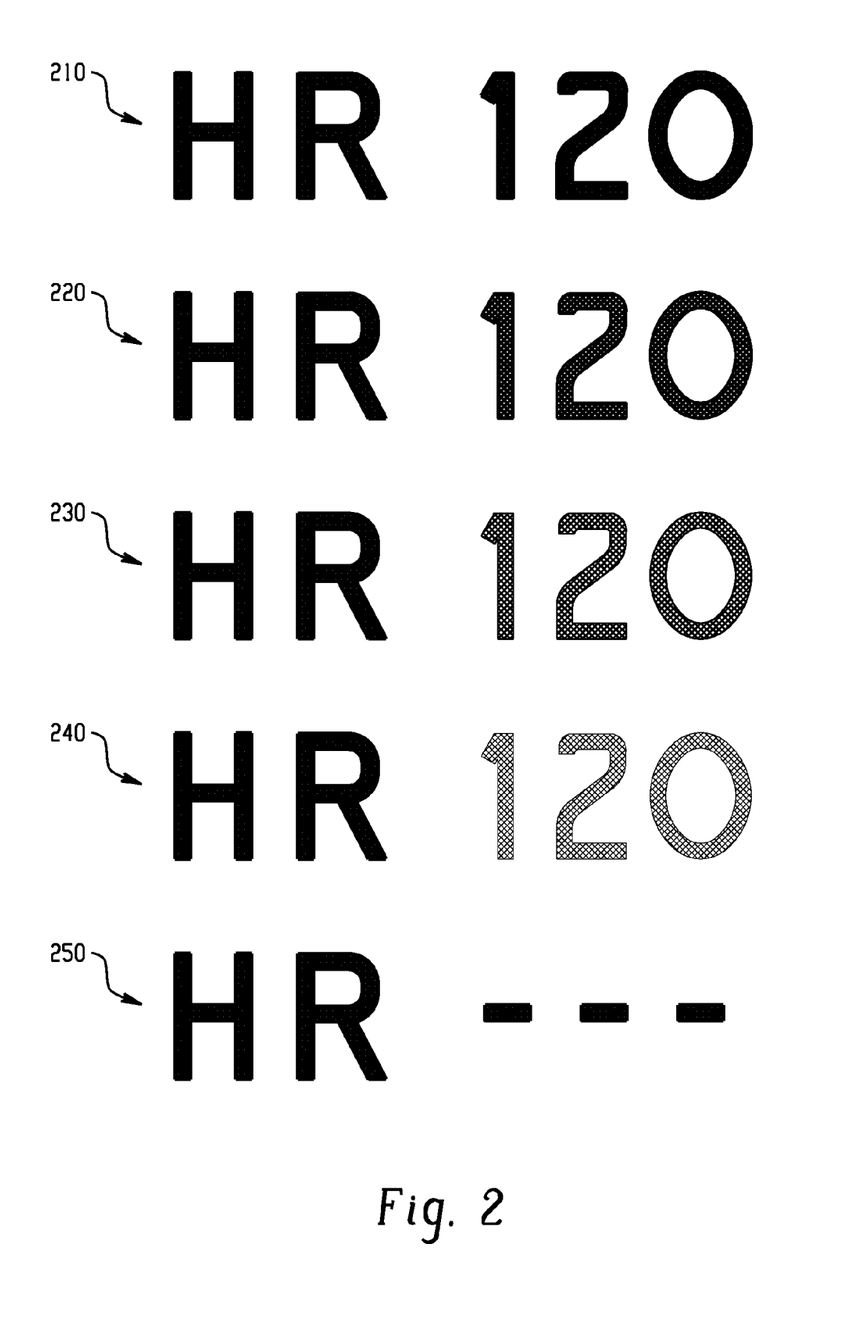
FIG. 2 illustrates fading in intensity to indicate parameter age.

In the embodiment of FIG. 2, a medical reading indicates the age of the displayed data by altering the intensity of the displayed numbers. In the present example, the most recent value is one that is less than 15 minutes old and the most recent value is the most intense, most brightly illuminated reading 210. As the readings age, the intensity decreases such that the reading which is more than 15 minutes old but less than 30 minutes old the displayed reading number 220 is less intense than the previously mentioned reading. Similarly, a reading 230 that is more than 30 minutes old but less than 45 minutes old is less intense than the previously mentioned reading, while a reading 240 that is more than 45 minutes old but less than 60 minutes old is less intense than the previously mentioned reading so as to be almost invisible. Finally, when the reading is more than 60 minutes old, the displayed completely disappears and is replaced by a symbol indicative of no current reading, such as but not limited to a dashed line 250. The times herein are given as an example and other lengths of time could be used. The device would function in substantially the same manner whether the readings were in seconds, minutes, hours, or days and the like.

Figure 3:
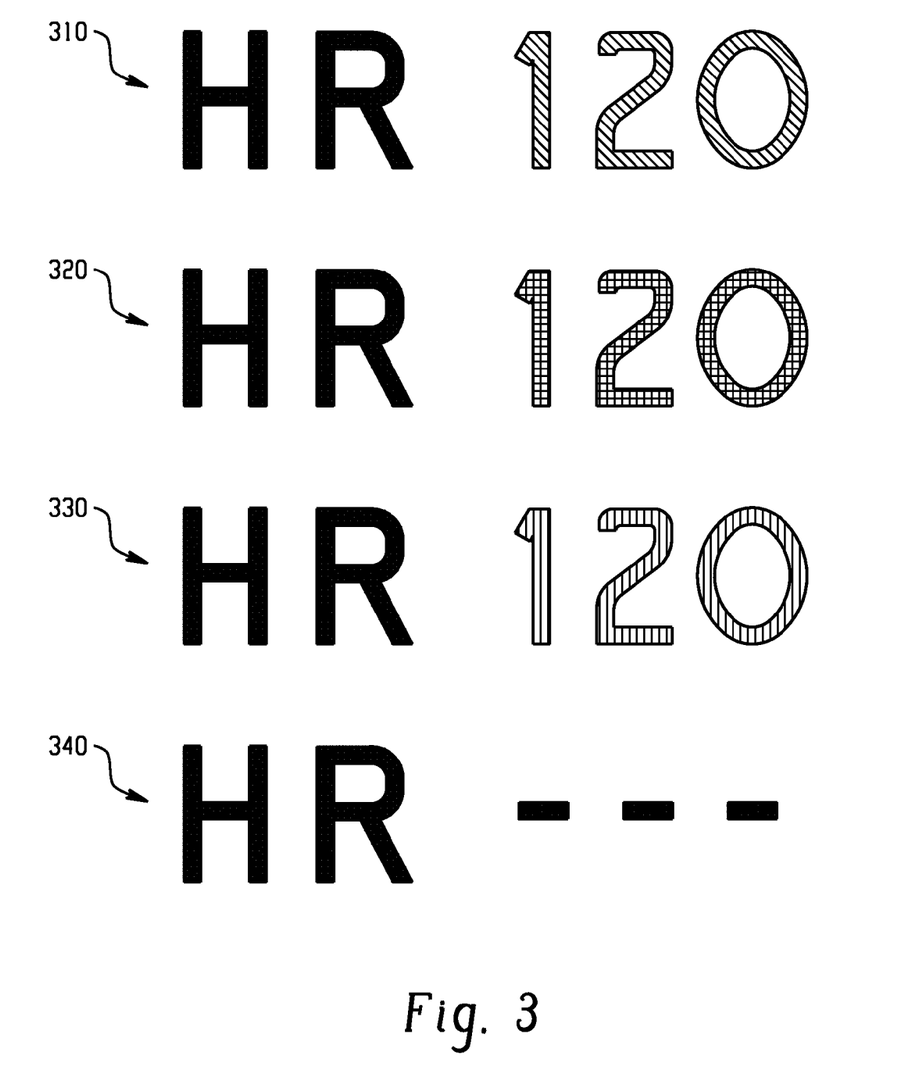
FIG. 3 illustrates a changing color to indicate parameter age.

In the embodiment of FIG. 3, the aging of the readings is represented not by the fading of the intensity of the readout, but by a change in color of the readout. The change of color functions analogously to fading in intensity of the previously recited disclosure. Thus green 310 could represent less than 15 minutes, yellow 320 could represent more than 15 and less than 30 minutes, and red 330 could represent more than 30 but less than 45 minutes, with the reading is more than 60 minutes old, the displayed completely disappears and is replaced by a symbol indicative of no current reading, such as but not limited to a dashed line 340. These colors are by way of example representative example, and any color could be assigned to any time frame. Any collection of colors, such as but not limited to pastels, earth tones, neon colors, primary colors and the like could be used to represent any time quantity such as, but not limited to, seconds, minutes, hours, or days. The color can change in discrete steps or can morph continuously. The color can be in discrete steps or continuous.

In one embodiment, the displayed reading value is initially presented at maximum contrast with the background. As the parameter ages, the color or intensity fades into the background color. For example, the color intensity decreases gradually to gray. Once the aging threshold is met, the data parameter is then removed.

The display of aperiodic measurements is aged in an intuitive way. In one embodiment, the content reading value fades as time elapses, such that the intensity of the data displayed dims. In another embodiment, the color assigned to the parameter in question fades to gray with time. This replaces a time or date stamp and reduces the clutter caused by including a date and time with the accompanying data.

Figure 4:
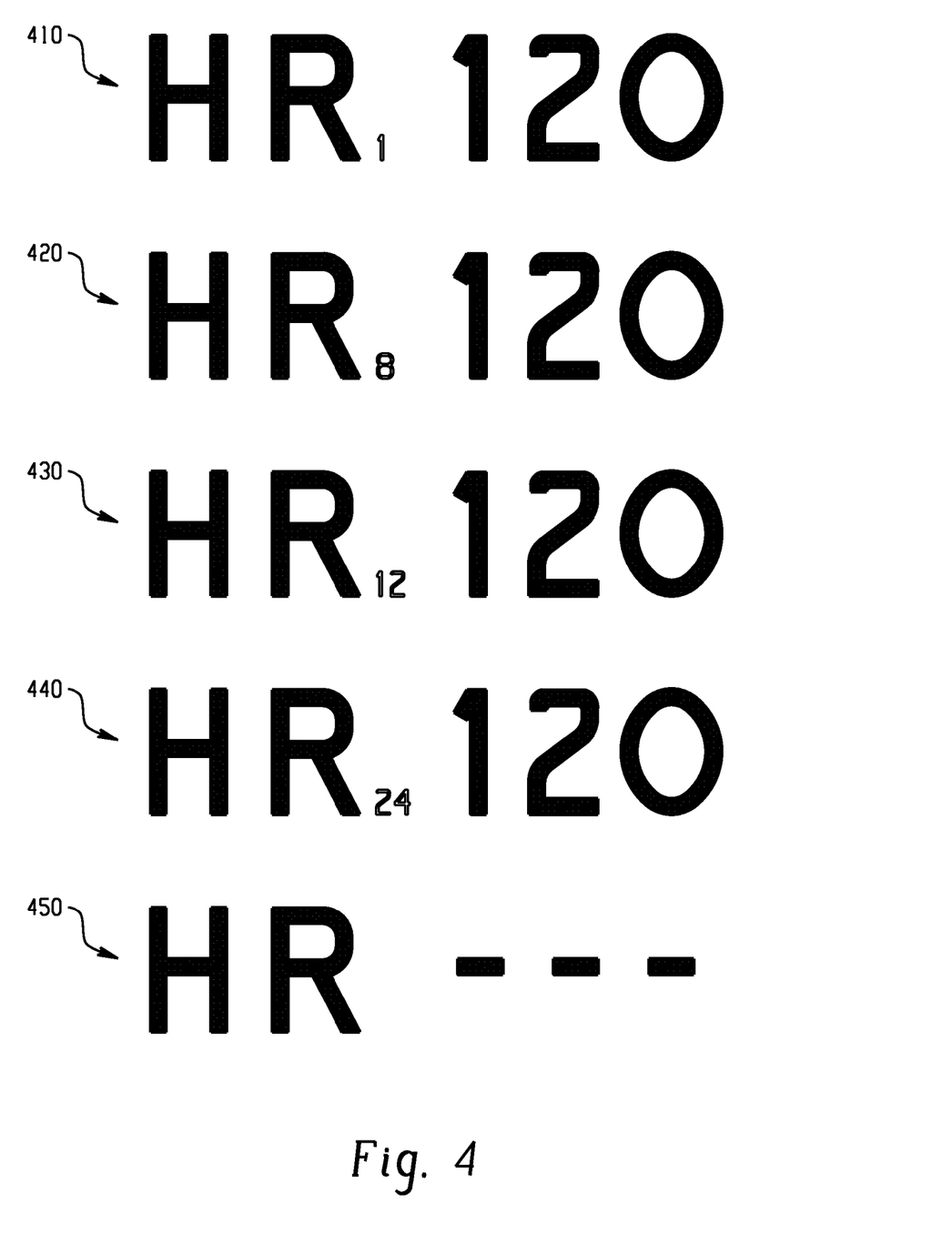
FIG. 4 illustrates subscript to indicate parameter age.

With reference to FIG. 4, in another embodiment the reading 140 includes a subscript 400. In one embodiment, the subscripts denote the nominal useful life of the aperiodic measurement over which it is aged. This reading value can fade or change color as disclosed above. Here, the presence of a 1 in subscript indicates that the reading has a useful life of 1 hour 410. A subscript of 8 indicates that the reading has a useful life of 8 hours 420. A subscript of 12 indicates that the reading has a useful life of 12 hours 430. A subscript of 24 indicates that the reading has a useful life of 24 hours 430. Finally, when the reading is more than 24 hours old, the displayed completely disappears and is replaced by a symbol indicative of no current reading, such as but not limited to a dashed line 450. These times are given by way of example and other lengths of time could be used in the device. The device would function in substantially the same way whether the readings were in seconds, minutes, hours, or days and the like. In another embodiment, the subscripts serve to indicate the aging or remaining useful life.

Figure 5:
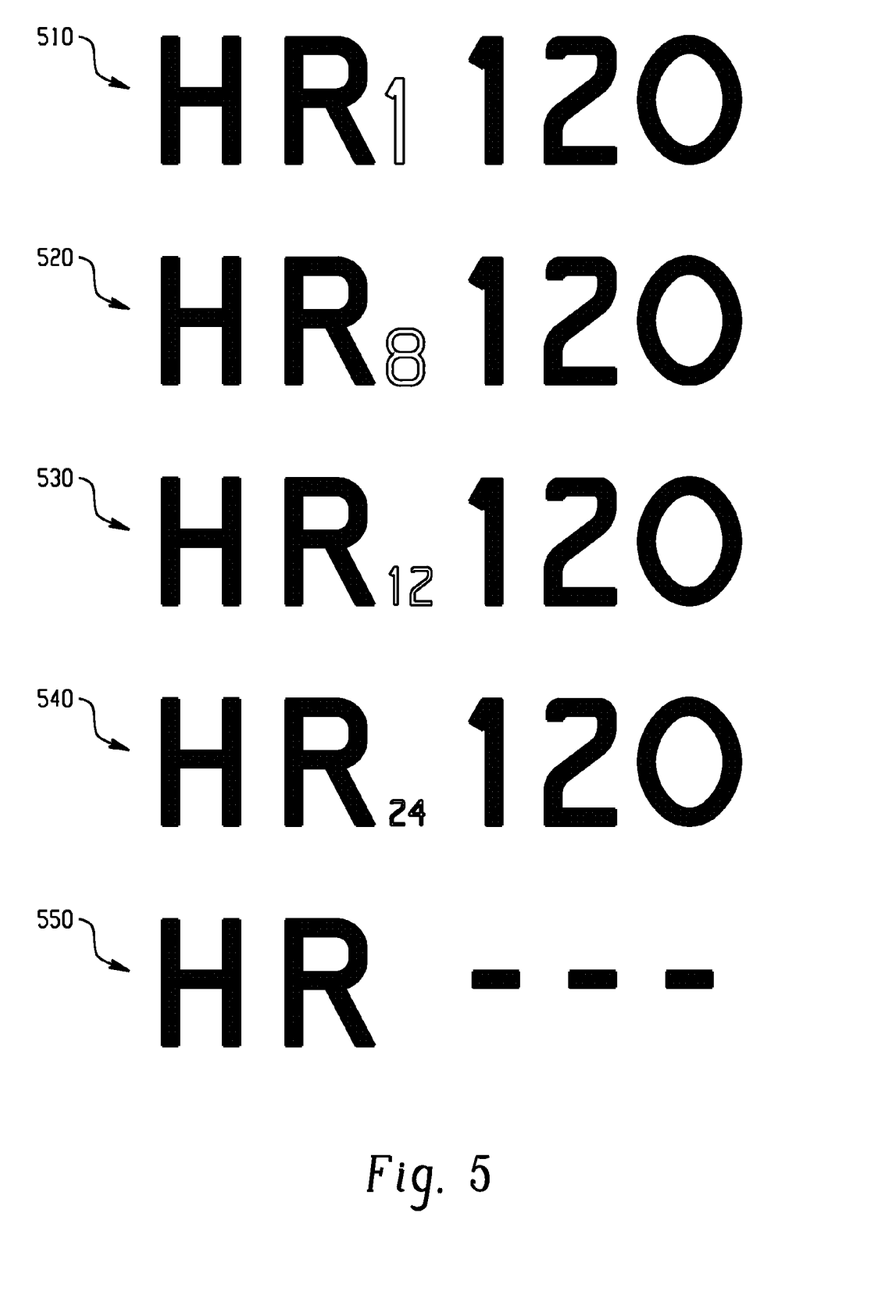
FIG. 5 illustrates changing the size of the subscript to indicate parameter age.

With reference to FIG. 5, the subscript indicates the age of the displayed reading value presented. The aging of the readings could also be represented by the size or shape of the subscript wherein the subscript is largest for a new reading 510 and shrinks to a smaller size 520, 530, 540 as the reading got older, or becomes more italic or less bold as the age progresses. Finally, when the reading is more than 24 hours old, the displayed completely disappears and is replaced by a symbol indicative of no current reading, such as but not limited to a dashed line 550.

Figure 6:
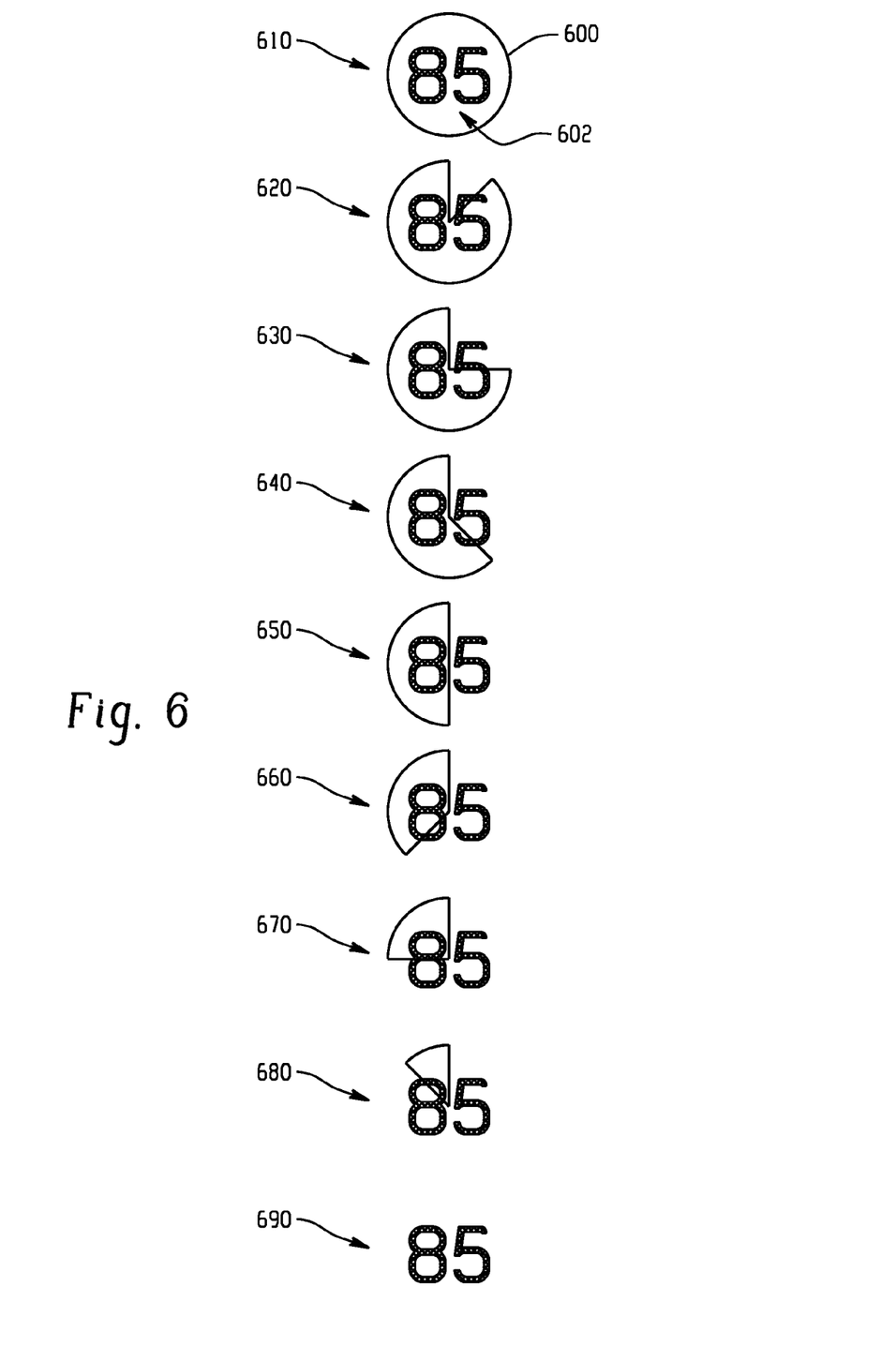
FIG. 6 illustrates progressive background change of a circle to indicate parameter age.

With reference to FIG. 6, another embodiment for displaying the age of the data parameter is presented. The display may include, but is not limited to, a circle 600 in which a data value 602 is disposed. The age of a display reading is conveyed through use of this graphical symbol. In one embodiment, a reading that is new or only a few minutes old is displayed in a full circle background 610. After a short time, such as but not limited to 7-10 minutes a small wedge is removed from missing from circle 620. As time progresses such as or about 15 minutes later, the wedge has grown to a quarter of the circle 630. Similarly, as the reading ages further to 22-25 minutes, the wedge continues to increase in size 640. Like a clock hands, at the 30 minute mark half of the background is missing 650. When the age exceeds 30 minutes, more of the circle is removed and the background is expanded 660. At the 45 minute age point three quarters of the background is missing 670. Finally, when the age is over 45 minutes, only a small of the circle would remain 680. The reading value and the circle would disappear completely after 60 minutes 690. The wedge icon thus emulates the movement of a clock hand.

Figure 7:
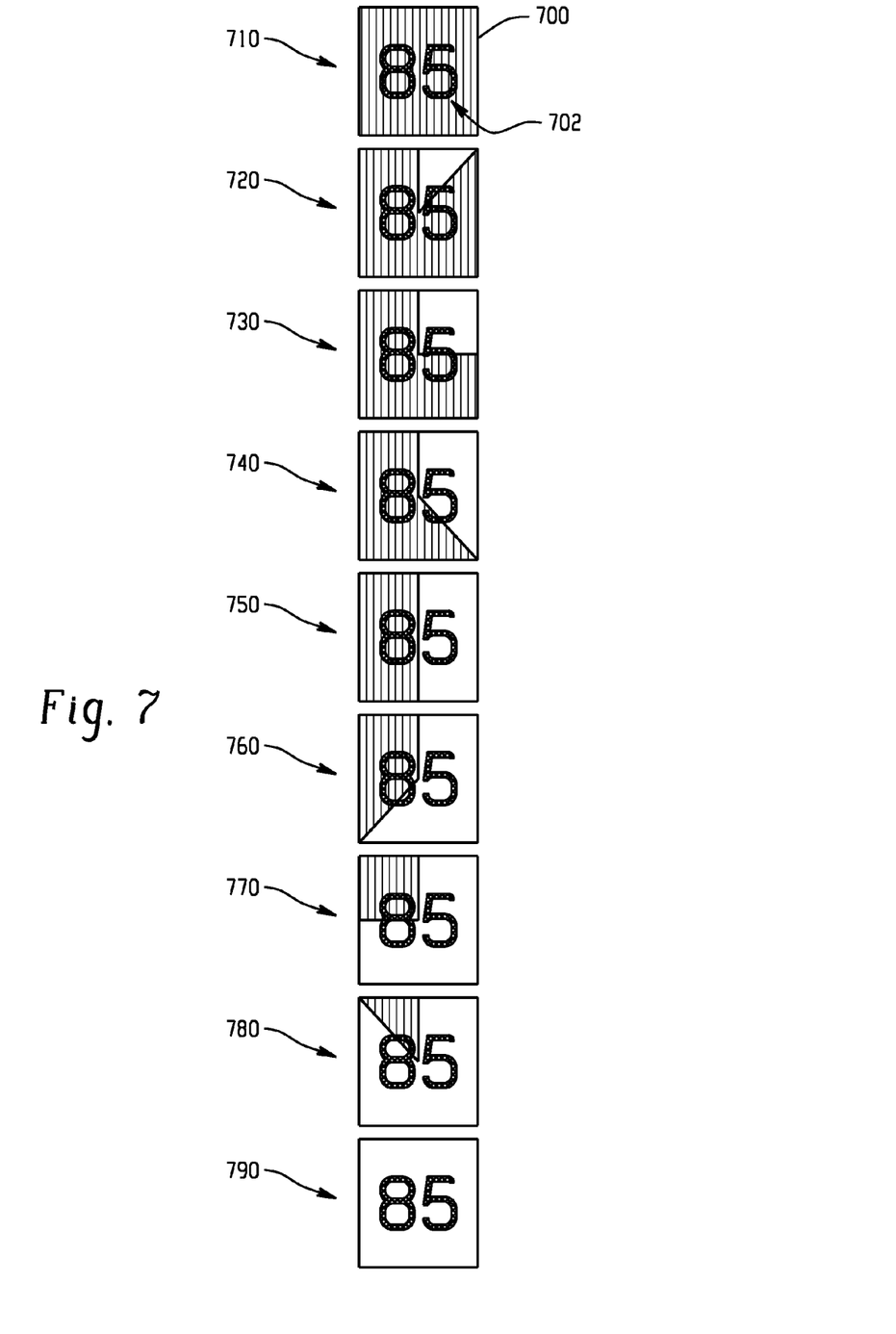
FIG. 7 illustrates progressive background change to indicate parameter age.

With reference to FIG. 7, another embodiment for displaying the age of the data parameter is presented. The display may include, but is not limited to, a box 700 in which a data value 702 of a second color is disposed. The age of a display reading is conveyed through use of this graphical symbol. In one embodiment, a reading that is new or only a few minutes old is displayed in a full background 710. After a short time, such as but not limited to 7-10 minutes a small wedge is removed 720. As time progresses such as or about 15 minutes later, the wedge has grown to a quarter 730. Similarly, as the reading ages further to 22 to 25 minutes, the wedge continues to increase in size 740. Like a clock hands, at the 30 minute mark half of the background is missing 750. When the age exceeds 30 minutes, more is removed and the background is expanded 760. At the 45 minute age point three quarters of the background is missing 770. Finally, when the age is over 45 minutes, only a small wedge remains 780. The reading value and the box disappear completely after 60 minutes 790. The wedge icon thus emulates the movement of a clock hand.

Figure 8:
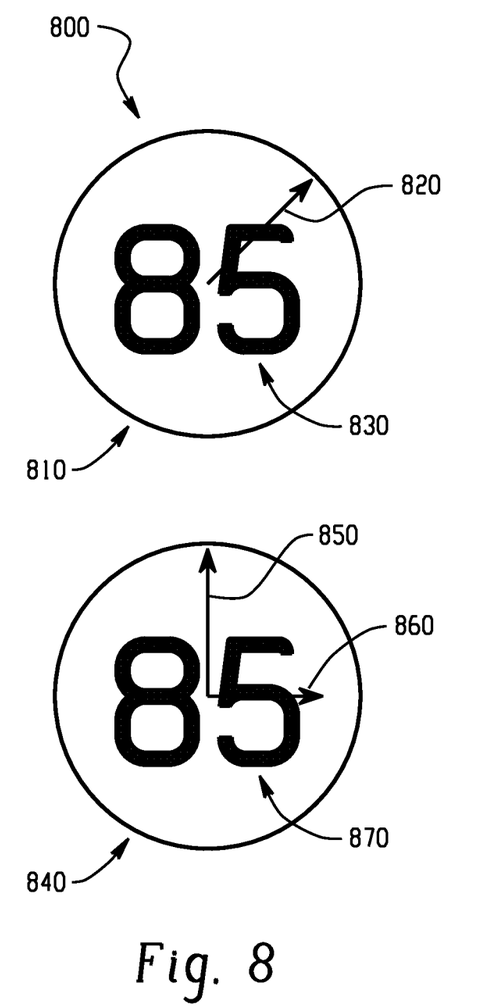
FIG. 8 illustrates the use of clock hands to indicate age of a parameter.

With reference to FIG. 8, an additional embodiment of the present application are disclosed which also uses a clock icons 800. As another embodiment of a clock 810, a clock hand 820 is used behind the reading value 830. Further, another suggested interface 840 may use a two handed clock to keep track of minutes 850 and hours 860 located behind the reading label or measurement value 870.

Figure 9:
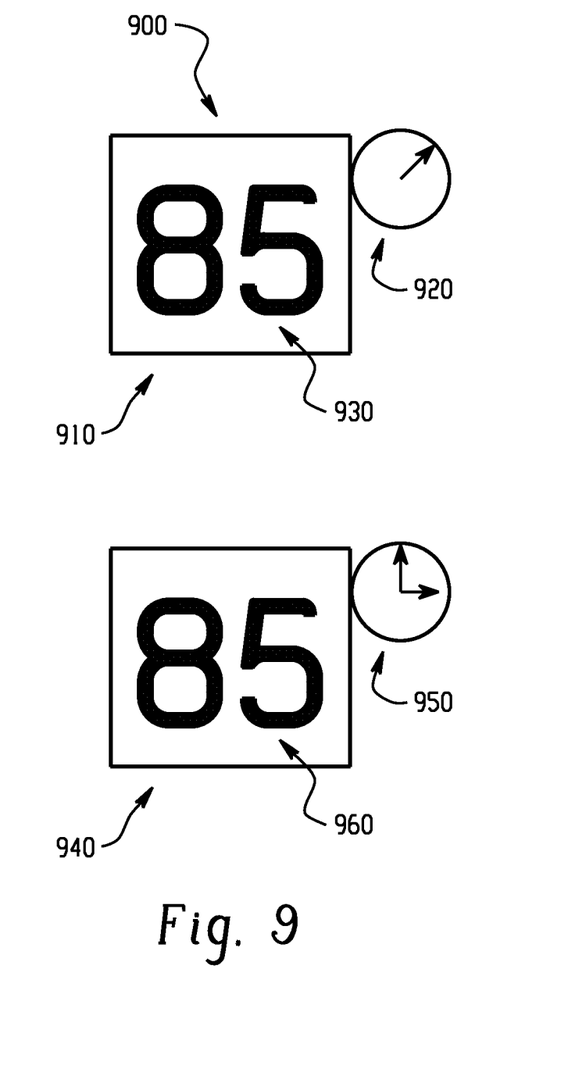
FIG. 9 illustrates a timer adjacent to the parameter reading.

With reference to FIG. 9, an additional embodiment to display the age of the reading 900. One embodiment 910 displays the age 920 adjacent the reading label or measurement value 930. Further, another suggested embodiment 940 displays the age using both hours and minutes using a two handed clock 950 adjacent to the reading label or measurement value 960.

Figure 10:
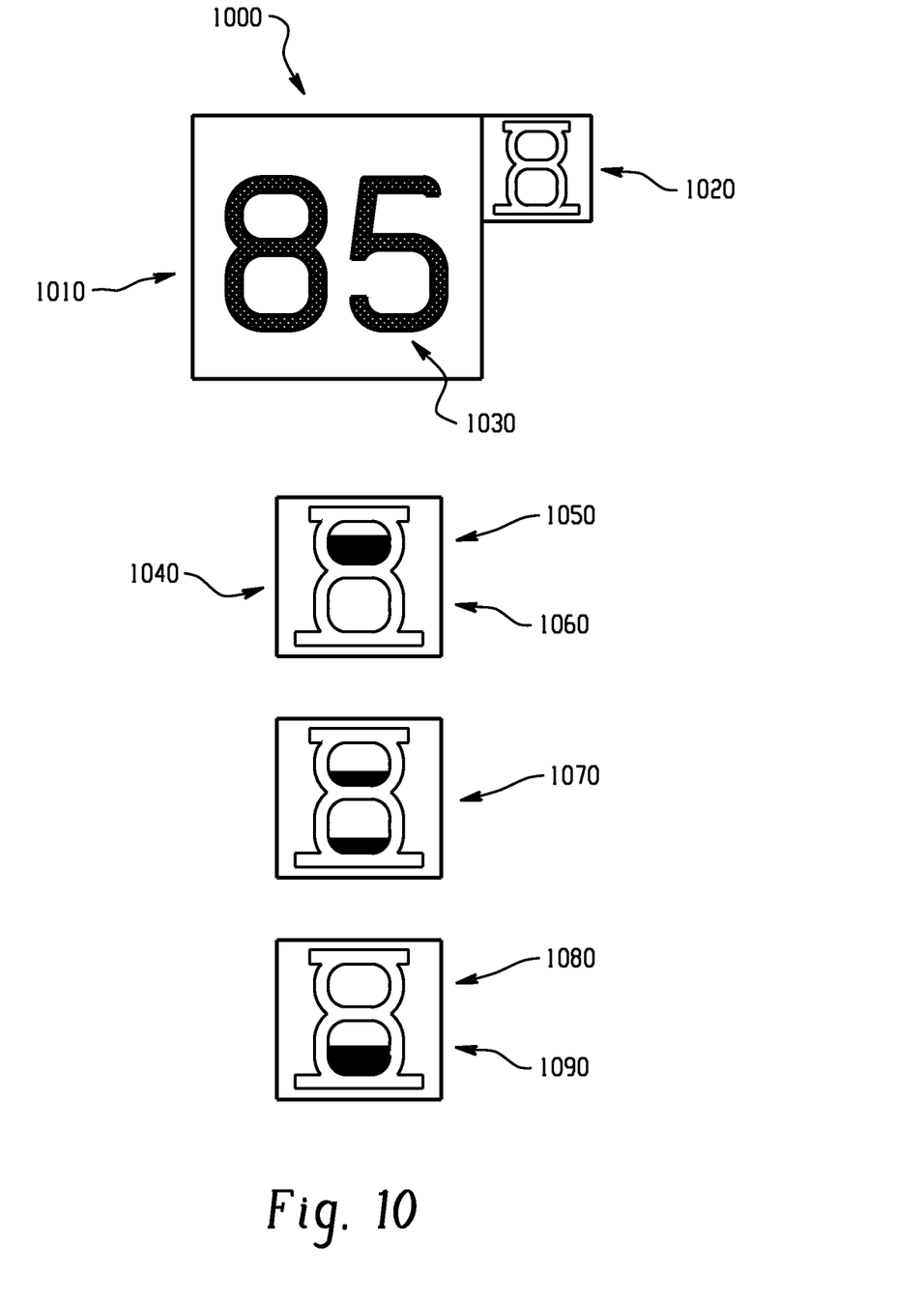
FIG. 10 illustrates the use of an hour glass as a timer mechanism.

With reference to FIG. 10, an additional embodiment 1000 presented displays another time-intuitive display 1010, such as but not limited to an hour glass 120, indicates the age of the reading data. Here the hour glass 1020 is located adjacent to the reading display 1030. The hourglass 1040 comprises an upper section 1050 and a lower section 1060. When the data reading value is new, the upper portion 1050 is darkened and the lower section 1060 is clear. As the reading ages 1070, the upper section reduces in volume and the lower section increases in volume by substantially the same amount of volume lost by the upper section. When the reading is about to expire, 1080, the volume of the upper section 1080 is empty and the volume of the lower section 1090 is substantially equal the original volume of the original upper section 1050. The display device functions in substantially the same way whether the readings were in seconds, minutes, hours, or days and the like. The hourglass can be displayed behind the reading.

Figure 11:
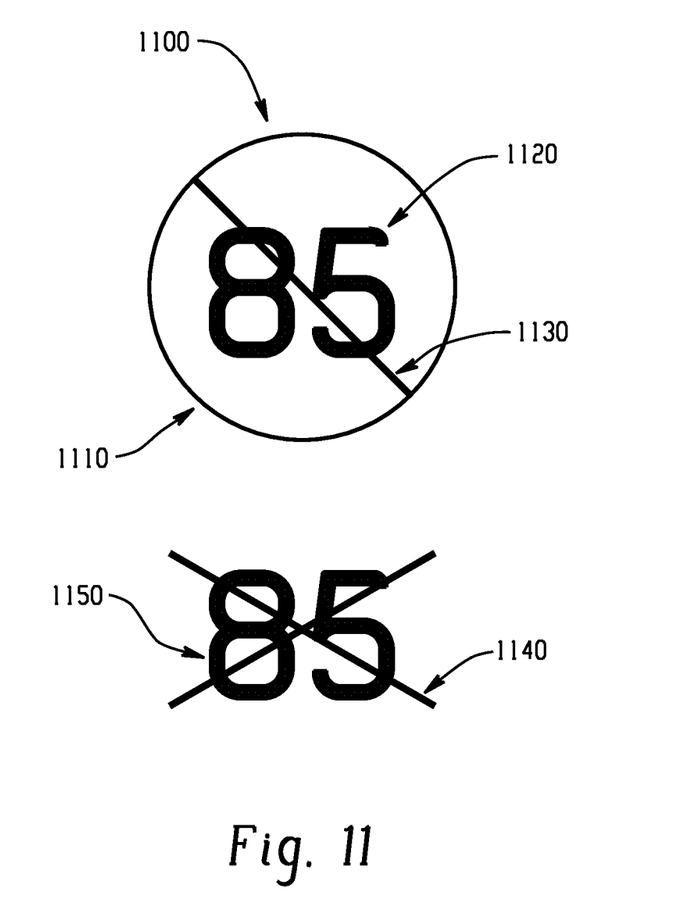
FIG. 11 illustrates the expired parameter reading being crossed out.

With reference to FIG. 11, another embodiment of the present application 1100 incorporates display of an icon to denote that the aperiodic measurement has expired. Icons include, but are not limited to, a slash-through, a "not" symbol 1110 comprised of a box or a circle 1110 with a slash 1130 superimposed over the reading value display 1120, or an "X" 1140 over the reading value 1150. Furthermore the time display of the measurement may also be dropped. Other icons which retain the label to denote that such a measurement should be there rather than merely eliminating the label or the reading value are also contemplated. Both the reading value displayed and the icon symbol over the reading value can be the same color or different colors, where the reading value may be darker or lighter than the icon symbol.

Furthermore, the indicators presented herein including the fading change in intensity, the change in color, use of a subscript, or the changing background. Another changing graphical symbol may be combined in any manner to signify the age of a data parameter reading.

Figure 12:
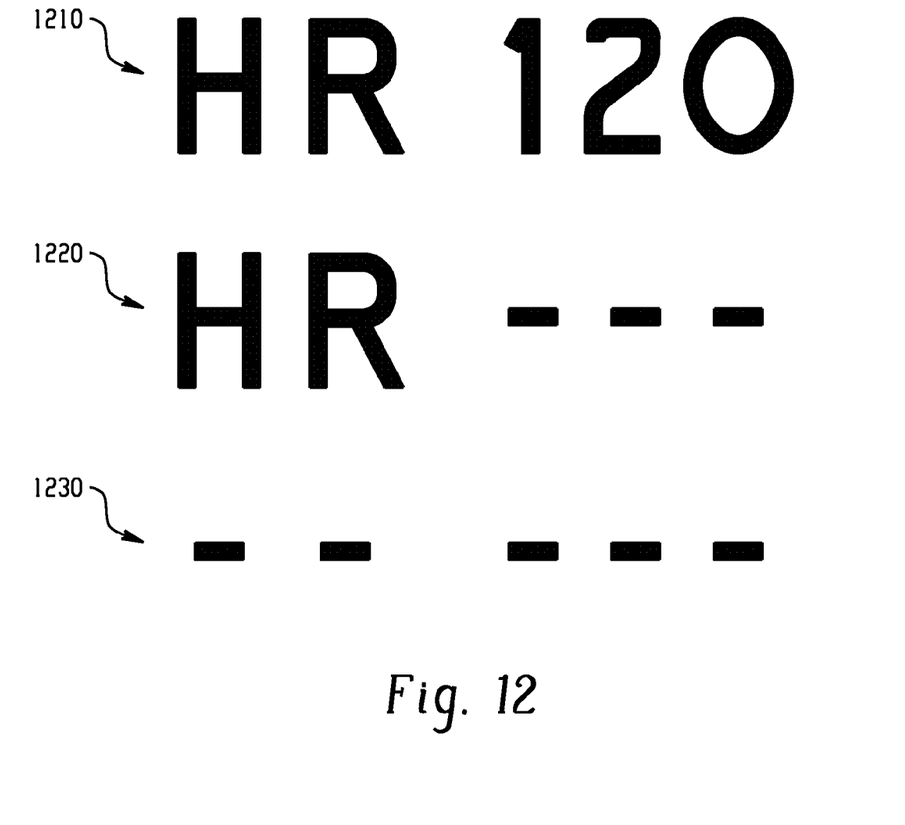
FIG. 12 illustrates the value has expired by substituting three dashes for numbers.

With reference to FIG. 12, an expired value may be indicated by the replacement of the numerical value or the alphanumeric characters with dashed line. A value is presented prior to expiration 1210 that conveys the reading to a user. When that reading is no longer valid, the numerical component of the reading may be replaced by dashed lines 1220. Another embodiment might also replace the alphanumeric characters that describe the reading 1230, such as 'FIR', in addition to also replacing the reading value such that the entire space formerly occupied by the reading is entirely replaced by dashes once the value has been deemed to have expired.

Figure 13:
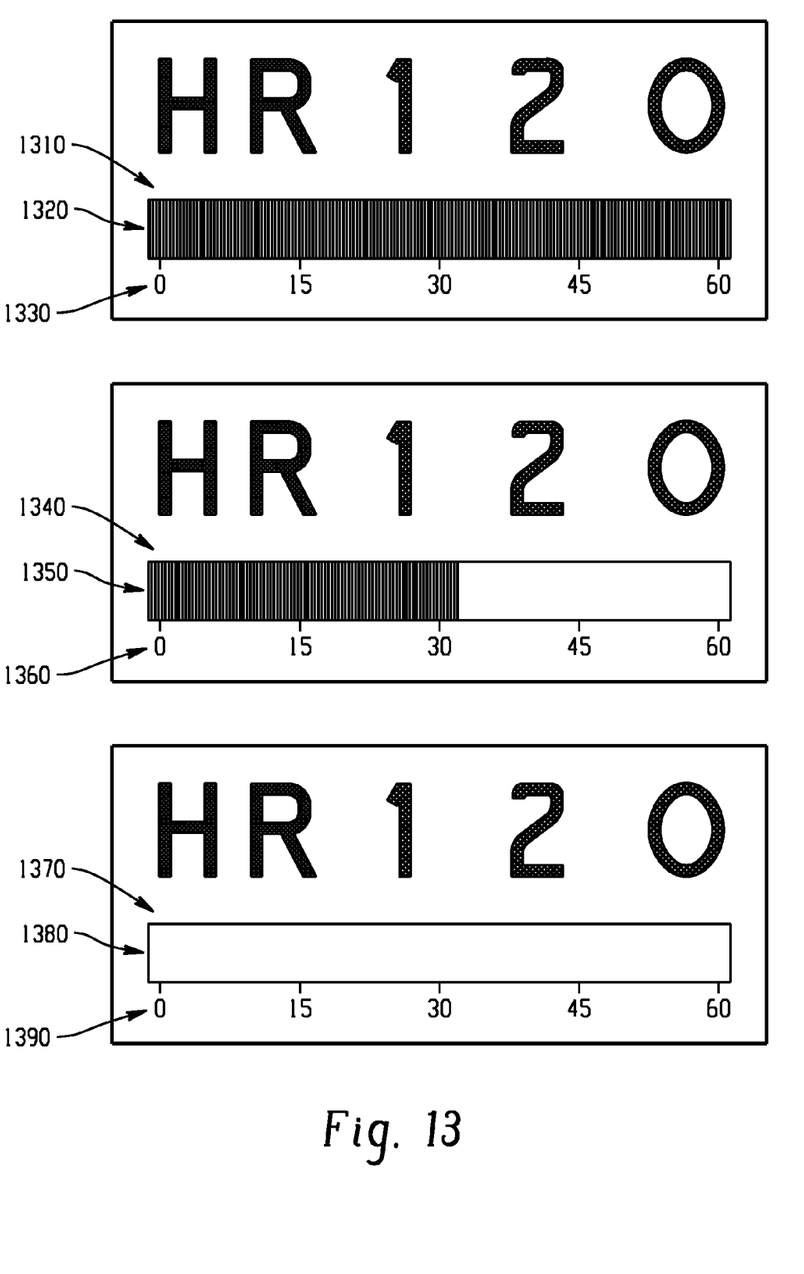
FIG. 13 illustrates a reading with a progress bar count down.

With reference to FIG. 13, an in progress countdown bar may also be employed to convey the time duration of the reading. Here a new alpha numerical medical reading 1310 would be accompanied by a graphical bar located above, below, or to the side of a medical reading value 1320. This bar may be fully darkened to indicate that the medical value is new and may transition to undarken the darkened potion as time passes and the medical value ages. A time legend 1330 may also be located substantially near the graphical bar.

As time passes and the medical value ages, 1340, the bar may transition from a fully darkened graphical display 1320 to a partially darkened graphical display 1350. The length of time that has passed or is remaining on the life of the medical value may be determined through use of an accompanying legend 1360. The degree to which the display is darkened will ideally correspond to the amount of time that has passed since the medical value was initially generated.

At the end of the useful life of the medical value 1370, the bar may be entirely undarkened such that there remains no shaded or darkened portion within the remaining outline of the previously darkened or shaded bar 1380. This unshaded or undarkened bar may also be accompanied by a legend 1390.

In an alternative embodiment, the graphical bar may begin life completely undarkened or unshaded, which would indicate that the accompanying medical value is new. In this embodiment, the graphical bar would gradually darken or fill up as time passes and the medical value ages such that a partially shaded or darkened bar would indicate an aging medical value. At the end of the useful life of the medical value, the graphical bar may be fully darkened so as to indicate that time is up for the life of the medical value and this value has expired.

In a further embodiment, the shading or darkening may be replaced by a change in the graphical bar's color, color shade, color intensity, shading pattern or shape. The color changing or darkening may proceed from right to left, from left to right, from center outward toward the edge, from the edge inward toward the center, from top to bottom, from bottom to top, from inside to outside, from outside to inside, diagonally from the upper right hand corner to lower left hand corner, diagonally from the upper right hand corner to the lower left hand corner, diagonally from the lower right hand corner to the upper left hand corner, diagonally from the lower right hand corner to the upper left hand corner, and the like.

The method, system and apparatus described herein may also incorporate a computer operable means including but not limited to a computer data input means, a computer display terminal for presenting data, a computer memory that may contain a database, and a network connection that may enable the method, system and apparatus to interact on a computer network system including but not limited to the Internet.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of displaying medical information, the method comprising: displaying a medical data value, the medical data value including:
    an icon image including an alphanumeric symbol quantifying the medical data value and at least one of a label thereof and;
        a subscript or superscript displayed adjacent to the alphanumeric symbol; and
    altering the icon image with time, such that the altered icon image is indicative of the medical data value and the medical data value's age;
    wherein the subscript or superscript is a medical data value's age indicator.

2. The method according to claim 1, wherein altering the icon image includes:
    changing a luminous intensity of at least a portion of the alphanumeric symbol and at least one of the subscript, a displayed background region to the medical data value, or the label.

3. The method according to claim 1, wherein altering the icon image further includes:
    changing a color of at least a portion of the one alphanumeric symbol and the at least one of the label thereof or the subscript.

4. The method according to claim 1, wherein the medical data value display further includes:
    displaying the image icon on a background; and
    changing at least one of size, shape, or color of the background with time.

5. The method according to claim 4, wherein the background emulates a clock as it changes with time by displaying one of:
    a circle or box divided into wedges that change color progressively analogous to a hand of a clock; and
    a circle with a clock hand that moves with time.

6. A method of displaying medical information, the method comprising:
    displaying a medical data value;
    altering the displayed medical data value with time, such that the displayed medical data value is indicative of the medical data value and the medical data value's age;
    displaying the medical data value or a label thereof on a background; and
    changing at least one of size, shape, or color of the background with time;
    wherein the background emulates a clock as it changes with time;
    wherein the background emulates the clock by displaying one of:
    a circle or box divided into wedges that change color progressively analogous to a hand of a clock; or
    a circle with a clock hand that advances with time.

7. The method according to claim 1, wherein the subscript or superscript includes:
    one of clock or hourglass icon adjacent to the alphanumeric symbol.

8. The method according to claim 1, further including:
    modifying the subscript or superscript with time to indicate an age threshold.

9. The method according to claim 1, further including:
    terminating displaying the medical data value in response to reaching an age threshold.

10. The method according to claim 1, wherein the medical data value is a non-continuously measured physiological parameter of patients which is displayed on a medical monitor.

11. A display apparatus which is controlled to perform the method according to claim 1.

12. A computer readable medium programmed with software which when implemented by a processor controls a monitor to perform the method of claim 1.

13. An apparatus for displaying a medical data value and a label thereof, the apparatus comprising:
    a human readable display device;
    a processor programmed to control the display device to:
        display at least one alphanumeric symbol quantifying the medical data value obtained from an electric device and the label;
        alter an icon image displayed with the at least one alphanumeric symbol with time;
        change a luminous intensity or color of the displayed alphanumeric symbol and the label and;
        display a subscript or superscript adjacent to the alphanumeric symbol and the label to indicate an age threshold,
        such that the displayed alphanumeric symbol or the label is indicative of the medical data value and medical data value's age.

14. The apparatus according to claim 13, wherein the medical data value represents a physiological parameter of a patient and further including:
    at least one of physiological parameter sensor for sensing a physiological parameter of the patient.

15. A display for displaying medical information, the system comprising:
    a computer operable video display terminal;
    a processor programmed to control the computer operable video display terminal to display:
        at least one alphanumeric symbol quantifying a medical data value, the medical data value representing a physiological parameter of a patient sensed by at least one physiological parameter sensor; and
        at least one graphical element conveying an age of the medical data value;
        wherein the at least one graphical element is at least one subscript or superscript adjacent to the at least one alphanumeric symbol.

16. The display according to claim 15, wherein the age of the medical data value is conveyed through change in color of at least a portion of the at least one alphanumeric symbol.

17. The display according to claim 15, wherein the age of the medical data value is conveyed through change in intensity of at least a portion of the at least one alphanumeric symbol.

18. The method according to claim 1, wherein the label thereof includes a medical data value progress countdown bar.

19. The display according to claim 15, wherein the at least graphical element includes a label indicating the age of the medical data value.

* * * * *